United States Patent
Giveen

[19]

[11] Patent Number: 6,016,764
[45] Date of Patent: Jan. 25, 2000

[54] REMOVABLY ATTACHABLE AUTOMATIC SQUEEZE BOTTLE UTILIZATION CYCLE COUNTING DEVICE

[76] Inventor: Samuel Charles Giveen, 1220 Chestnut St., Apt. A, Alameda, Calif. 94501

[21] Appl. No.: 09/256,508

[22] Filed: Feb. 22, 1999

Related U.S. Application Data

[63] Continuation of application No. 08/866,896, May 30, 1997, Pat. No. 5,860,387.

[51] Int. Cl.[7] .............................. B67D 5/12; G01D 13/00; G09F 11/00
[52] U.S. Cl. ......................... 116/284; 116/285; 116/315; 206/277; 206/459.1; 215/230; 222/27; 222/32
[58] Field of Search ..................................... 116/223, 284, 116/285, 308, 309, 311, 312, 315; 206/277, 459.1; 215/203, 230, DIG. 3; 235/66, 85 R; 222/27, 32, 44, 38

[56] References Cited

U.S. PATENT DOCUMENTS

| | | | |
|---|---|---|---|
| 2,636,469 | 4/1952 | McKay | 116/312 |
| 3,735,099 | 5/1973 | Herr | 235/91 R |
| 4,037,719 | 7/1987 | Perlmutter | 206/266 |
| 4,207,982 | 6/1980 | Maxwell et al. . | |
| 4,528,933 | 7/1985 | Allen . | |
| 4,548,157 | 10/1985 | Hevoyan . | |
| 4,565,302 | 1/1986 | Pfeiffer et al. | 222/38 |
| 4,634,012 | 1/1987 | Kelley . | |
| 4,817,822 | 4/1989 | Rand et al. | 222/38 |
| 5,174,473 | 12/1992 | Marelli | 222/38 |
| 5,280,834 | 1/1994 | Berkley . | |
| 5,356,012 | 10/1994 | Tang et al. . | |
| 5,860,387 | 1/1999 | Giveen | 116/285 |

*Primary Examiner*—Hezron Williams
*Assistant Examiner*—Willie Morris Worth

[57] ABSTRACT

A removably attachable automatic squeeze bottle utilization cycle counting device comprises a squeeze bottle, a nozzle, a removable nozzle cap for isolating the nozzle from the outside environment and a hinged mechanism which attaches onto the squeeze bottle and nozzle in a removable manner. This mechanism locates the nozzle cap relative to the nozzle and indicates the number of times the nozzle cap has been removed or replaced in a given cycle. The mechanism comprises upper and lower clips for removably attaching the mechanism to the bottle and nozzle cap, a rotatable part, a set of symbols, an indicator and mechanical means for indexing the rotatable part. Each time the nozzle cap is removed, or each time it is replaced, the rotatable part is automatically indexed to the next sequential position. This arrangement allows tracking of compliance with a prescribed regimen which includes using the contents of the squeeze bottle, while decreasing the risk of digital microbial contamination of the nozzle and the contents of the bottle.

4 Claims, 2 Drawing Sheets

REMOVABLY ATTACHABLE AUTOMATIC SQUEEZE BOTTLE UTILIZATION CYCLE COUNTING DEVICE

A continuation of patent application Ser. No. 08/866,896, filed May 30, 1997 which has been previously accepted for allowance and assigned U.S. Pat. No. 5,860,387, Jan. 19, 1999.

BACKGROUND—FIELD OF INVENTION

The present invention relates to liquid containment and dispensing devices which are handheld and resealable, as well as to devices which comprise use-cycle counting mechanisms.

BACKGROUND—DISCUSSION OF PRIOR ART

The uses of liquid pharmaceutical agent dispensing bottles

Many liquid pharmaceutical agents prescribed for repeated therapeutic use and solutions used for the maintenance of eye contact lenses are distributed in plastic squeeze bottles. Such an agent is typically dispensed by the user through an orifice, which is covered by a screw-on or snap-on cap when not in use.

The necessity of keeping track of use cycles with liquid pharmaceutical and eye contact lens liquid agents End users of eye contact lens solutions and therapeutic eye drops are faced with the necessity of keeping track of the number of dispensing cycles performed in a given period of time, or the total number of executions of an associated activity. As an example, therapeutic eye drops may be prescribed for use four times per day. As a second example, disposable soft eye contact lenses are often prescribed for 14 days of wear with nightly removal, cleaning and storage prior to disposal. Wearers must keep track of the total number of days during which a particular pair of such lenses has been worn. These counts are often important to the management of existing diseases and to the prevention of new disease states. Keeping count mentally is a method offering poor accuracy.

Devices which allow use cycle tracking for pharmaceutical agents and cigarettes

A number of mechanical devices are known which allow patients to keep track of their utilization of pills. U.S. Pat. Nos. 4,528,933 to Allen, July 1985, 4,634,012 to Kelley, January, 1987 and 5,356,012 to Tang and Yang, October, 1994 describe pill bottles with fully removable caps in which automatic indexing devices are incorporated for the purpose of tracking dispensing cycles. These cannot be used for dispensing liquids in a controlled fashion.

U.S. Pat. No. 2,636,469 to McKay, January, 1952, describes a capsule dispenser which indicates the fact that the container has been opened and a capsule has been removed during sequential time periods. McKay's device differs from the current invention in that it has a cap, which slides linearly and is held captive on the container. It has neither facility for sealing, nor a nozzle, nor a hinged nozzle cap and cannot be used for dispensing liquids in a controlled fashion.

U.S. Pat. No. 4,817,822 to Rand et al, April, 1989, describes a use cycle counting device attached to an aerosol bottle such as those used for dispensing inhalable atomized medications. The device of Rand et al differs from the current invention in that it uses a pressurized aerosol canister rather than a manually deformable squeeze bottle. Indexing is by linear compression of the nozzle toward the bottle, rather than detachment of a hinged nozzle cap in an arcuate manner. The device of Rand et al has neither a hinge nor an attached nozzle cap for the isolation of the nozzle.

U.S. Pat. No. 3,735,099 to Herr, May, 1973, describes a use cycle counting cigarette lighter wherein opening and closing the cover serves to index a ratchet wheel. Herr's device differs from the current invention in that it includes a rigid case rather than a manually deformable squeeze bottle, an aperture containing a wick rather than a nozzle and means for striking a spark.

U.S. Pat. Nos. 4,565,302 to Pfeiffer et al, January, 1986 and 5,174,473 to Marelli, December, 1992, describe use cycle counting devices attached to bottles of the type used for dispensing nasal sprays. These devices differ from the current invention in that they include piston pumps for expelling liquid contents rather than relying upon the generation of internal fluid pressure by squeezing a manually deformable squeeze bottle. Indexing is by linear compression of the collar toward the bottle, rather than detachment of a hinged nozzle cap in an arcuate manner. The device of Pfeiffer et al and the device of Marelli have neither hinges, nor attached nozzle caps, nor indexing means attached to the nozzle caps for the isolation of the nozzles.

U.S. Pat. No. 4,207,982 to Maxwell and Crisp, June, 1980, describes a pill bottle with an automatically indexing flip-top closure which remains attached to the bottle. It does not provide facility for incorporation of a fluid-tight seal and, likewise, cannot be used for dispensing liquids in a controlled fashion.

U.S. Pat. No. 4,037,719 to Perlmutter, July, 1987, describes a cigarette case which counts the number of dispensing cycles executed. It has a large opening through which solid objects can be dispensed and has neither facility for containing liquid nor facility for dispensing liquid in a controlled fashion. It lacks a nozzle through which dispensing of a liquid may be modulated by varying the fluid pressure within the container.

A device with a manually rotatable element has been applied to a liquid dispenser as shown in U.S. Pat. No. 4,548,157 to Hevoyan, October, 1985. This device similarly depends upon manual operation and user diligence and ability in proper indexing, having no facility for automatic operation.

Devices which allow use cycle tracking for controlled use of eye contact lenses

A patient's memory is generally relied upon as assurance of proper dosing and dispensing of medications and use of eye contact lens solutions. Calendars and paper records are often recommended, but their utility is limited by the user's diligence and ability in keeping the records up-to-date. A contact lens storage case is known which provides a manually operated wheel, bearing a sequence of numerals to keep a running total of days of use, shown in U.S. Pat. No. 5,280,834 to Berkley, January, 1994. This device does not directly involve the dispensing of fluid through the nozzle of a manually deformable squeeze bottle. Effective use of the device depends upon the patient's diligence and ability in indexing the wheel exactly once for each daily cycle as the device does not provide for automatic operation.

A squeeze bottle and cap assembly which bears a ratcheting numbered wheel to indicate the number of opening and closing cycles performed is described in U.S. Pat. No. 5,860,387 to Giveen, of which this application is a continuation.

The present invention is similar in function to this device. It differs in that the present invention is a separate hinged nozzle cap control and counting device which attaches onto an existing cap and nozzle assembly, rather than being a mechanism integrated into the nozzle cap apparatus.

BACKGROUND—DISCUSSION OF PROBLEMS ADDRESSED BY THE INVENTION

The difficulty encountered by sporadic contact lens users in tracking use cycles In addition to tracking the use of disposable contact lenses worn on a waking-hours-only basis, generally used with a recommended fourteen-day replacement cycle, counts of days of use must be kept in the performance of periodic enzymatic contact lens cleanings, most often recommended on a seven day of wear cycle. These schedules are less difficult to keep when lenses are used consistently on consecutive days. Patients who use their lenses less frequently than every day, however, often have only a vague idea of how many uses a particular pair of contact lenses has undergone. Since less frequent contact lens disposal presents a lower immediate financial cost to the patient, these patients tend to err in the direction of wearing their lenses for more days than prescribed, or of enzymatically cleaning their lenses less frequently than prescribed. As this can negatively affect the patient's eye health as well as decrease the volume of materials sold, compliance with such regimens is a cause of much concern in the eye care and eye contact lens industry.

Regimen noncompliance by patients using therapeutic eye drops

While necessary for disease management, therapeutic eye drops such as those used in glaucoma therapy, are often irksome to patients, expensive to purchase and may induce undesirable physiological side effects. Many patients' compliance with eye drop instillation frequency instructions is compromised by waning motivation, failing memory and lack of adequate attention. Perhaps the best example is patients under topical medical therapy for glaucoma, generally a disease of the elderly. These patients very frequently comply incompletely with their prescribed regimens of, generally, one to four eye drop instillations per day for life. Such noncompliance is typically unintentional and contributed to by the negative influences previously mentioned. When the patient is under an appropriate regimen, the result of such noncompliance may be a chronic elevation of fluid pressure within the eye and otherwise avoidable permanent loss of visual function.

The inadvertent contamination easily allowed by commonly used cap designs

Hinged bottle caps are well known in the prior art, but are not commonly used in packaging the aforementioned eye contact lens solutions and topical liquid medical eye drops. Currently used snap-on nozzle caps which are tethered to main bottle caps, such as those commonly used on eye contact lens maintenance solutions, are designed in such a way as to make the avoidance of digital contamination of the nozzle, during manual removal and replacement of the nozzle cap, difficult. This configuration also allows contact between the lower edge of the nozzle cap, which is often touched with the fingers during removal, and the nozzle, due to indefinite relative positioning of the nozzle and the nozzle cap. A screw-on nozzle cap is frequently set down upright on an unsanitary surface and, subsequently, its lower surface is easily touched to the nozzle during removal and replacement, allowing contamination of the nozzle and the contents. In addition, in part due to their small size, snap-on nozzle caps can be quite difficult to remove, sometimes resulting in them being left off entirely or removed with the user's teeth, either of which actions degrades hygiene, thereby increasing the risk of ocular infection.

SUMMARY DESCRIPTION OF THE INVENTION

The present invention is a device, to be attached to a liquid containment and dispensing apparatus, such as those used with eye contact lens maintenance solutions, which are stored and distributed in manually deformable squeeze bottles. This invention facilitates sanitary execution of the containment and dispensing functions of the commonly used apparatuses. By means of a hinge, it provides positive relative location of the nozzle and the nozzle cap, thereby decreasing the risk of contamination of the contents. Finally, by use of a mechanical rotary indexing mechanism which bears icons, it provides information to the user regarding the number of times the apparatus has been used during a given cycle, to assist the user in complying with a prescribed regimen.

In particular, the invention is a resealable liquid containment and dispensing apparatus, for the automatic recording of the number of controlled serial dispensings of liquid, performed or yet to be performed, in a given cycle, comprising a necked, manually deformable bottle member; a bottle cap member, attached and sealed to said bottle member; a nozzle member, formed on said bottle cap member and a hole passing through said nozzle member and said bottle cap member; a nozzle cap member, removably sealable onto said nozzle member, providing, while said nozzle cap member is sealed onto said nozzle member, the isolation of said nozzle member and said liquid contents from the outside environment, and allowing, when said nozzle cap member is removed from said nozzle member, the controlled expulsion of said liquid contents through said nozzle member by the generation of positive internal fluid pressure, through manual deformation of said bottle member; a lower clip member, removably attached to one of said bottle member and said bottle cap member; an upper clip member, removably attached to said nozzle cap member; a hinge, hinging said lower clip member to said upper clip member, permitting controlled removal of said nozzle cap member from and resealing of said nozzle cap member to said nozzle member in an arcuate path; a journal member, protruding from one of said lower clip member and said upper clip member; a disc member, rotatably retained upon said journal member; a ratchet tooth set, comprising multiple ratchet teeth, projecting from said disc member, said ratchet teeth positioned on equal angular spaces, the number of said spaces being at least equal to the number of said ratchet teeth present; forward indexing means protruding from the other of said lower clip member and said upper clip member as does said journal member, said forward indexing means resting between two teeth of said ratchet tooth set while said nozzle cap member is sealed to said nozzle member, providing forward rotation of said disc member through an angle equal to one of said equal angular spaces when said nozzle cap member is lifted away from and returned onto said nozzle member so as to allow free expulsion of said liquid contents from said nozzle and subsequent resealing; means to prevent reverse rotation protruding from the same one of said lower clip member and said upper clip member as does said journal member, said means to prevent reverse rotation resting between two teeth of said ratchet tooth set; indicating means comprising a circularly arranged set of equally spaced sequential symbols and an indicator, said indicating means being on the surface of said disc member and one of said lower clip member and said upper clip member.

OBJECTS AND ADVANTAGES

Accordingly, several objects and advantages of the present invention are to provide the user of a resealable liquid containment and dispensing apparatus, with a secondary apparatus for controlling the movement of the nozzle cap and for counting the number of sequential dispensing cycles executed, which provides an improvement in the sanitary enclosure of said liquid contents and automatically informs the user of the number of times the apparatus has been, or has yet to be, either opened or closed or both, as a running total or relative to a given time period, or by association, the number of times another related activity has been performed, to reduce the user's dependence upon memory in complying with medical therapeutic regimens which utilize liquid pharmaceutical agents and in complying with eye contact lens maintenance regimens, thereby improving the accuracy of compliance with prescribed regimens, to simplify and make more convenient the task of keeping track of the number of times the containment apparatus has been either opened or closed or both, as a running total or relative to a given time period, or by association, the number of times another related activity has been performed.

to facilitate manual removal and replacement of the nozzle closure, and to decrease the risk of contamination of the nozzle, thereby decreasing the risk of contamination of the contents of the bottle and of the expelled liquid, with a resultant decrease in the risk of ocular infection.

Further objects and advantages of the present invention will become apparent from a consideration of the drawings and ensuing descriptions.

DRAWING FIGURES

FIG. 1A is a perspective view, sectioned to illustrate detail.

Figure 1A:
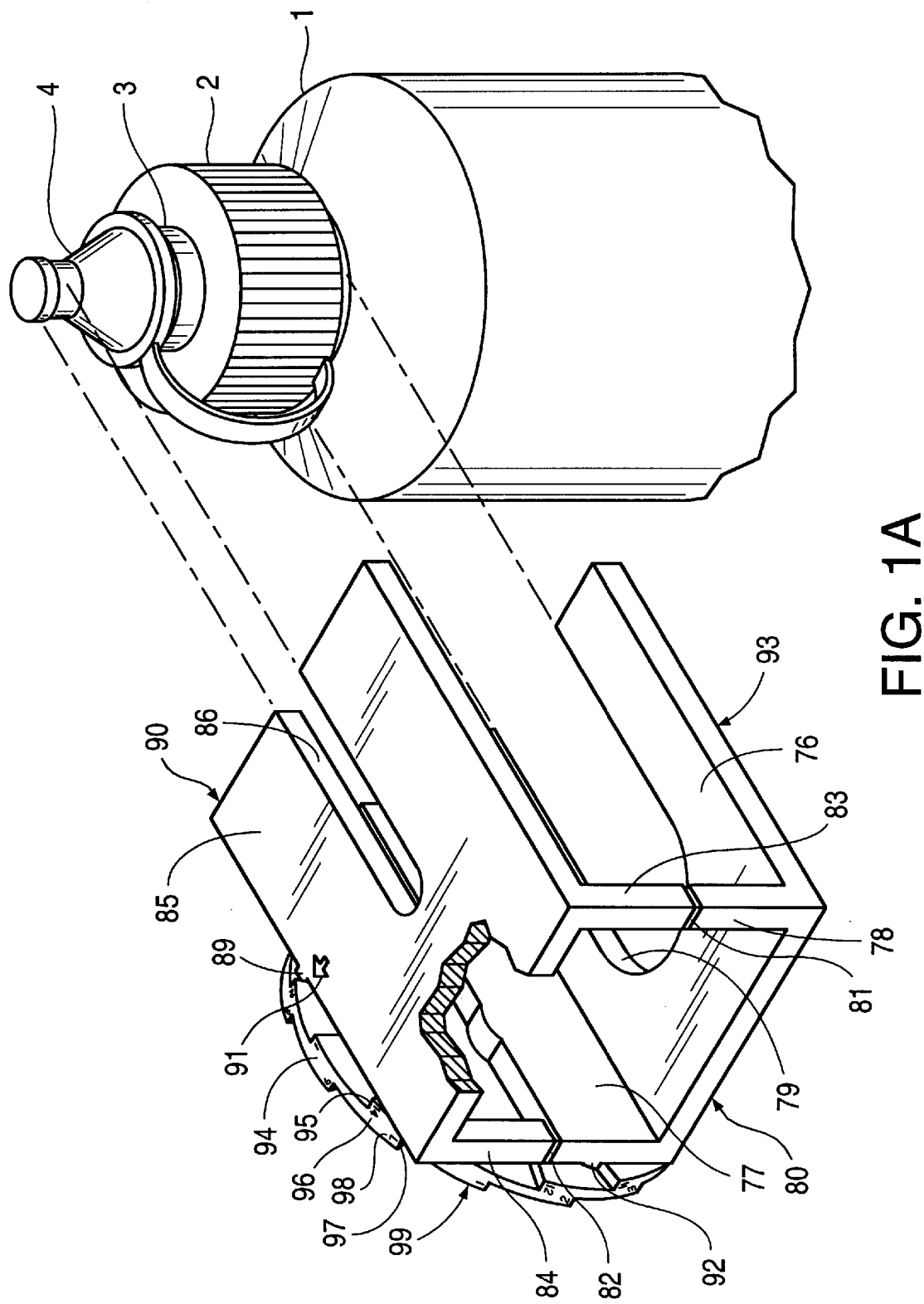
FIG. 1A depicts the preferred embodiment of the present invention, in which a counting mechanism is integrated into a device which can be clipped onto a separate bottle, cap, nozzle and nozzle cap assembly, this assembly being shown assembled, in the closed condition.

REFERENCE NUMERALS USED IN THE DRAWINGS bottle member 1
bottle cap member 2
nozzle member 3
nozzle cap member 4
lower attachment member 76
support wall 77
left lower leg 78
lower slot 79
lower clip member 80
left integral hinge segment 81
right integral hinge segment 82
left upper leg 83
right upper leg 84
upper attachment member 85
upper slot 86
journal member 87
retaining means 88
forward indexing means 89
upper clip member 90
indicator member 91
means to prevent reverse rotation 92
gripping unit 93
disc member 94
first ratchet tooth set 95
first set of equally spaced sequential symbols 96
second ratchet tooth set 97
second set of equally spaced sequential symbols 98
indicator disc member 99

DESCRIPTION OF THE PREFERRED EMBODIMENT—FIGS. 1A AND 1B

FIG. 1A is an assembly view with break-away sections illustrating the preferred embodiment of the invention. Included in FIG. 1A is a bottle apparatus of a familiar type, standard in the eye contact lens solution industry, comprising a necked bottle member 1, a bottle cap member 2, a nozzle member 3 and a nozzle cap member 4, to which the balance of the invention can be attached for unified operation.

A rectangular lower attachment member 76, comprising a left surface, a right surface, an upper surface, a front surface and a rear surface is oriented horizontally. A rectangular support wall 77, comprising a rear surface and an upper surface, protrudes upward from the upper surface of lower attachment member 76 adjacent to the right surface of lower attachment member 76. A left lower leg 78, comprising a rear surface and an upper surface, extends upward from upper surface of lower attachment member 76 adjacent to the junction of rear surface of and left surface of lower attachment member 76. A lower slot 79 lies in lower attachment member 76, open at the front surface of lower attachment member 76 and extending rearward, ending in a semicircular surface.

Lower clip member 80 comprises lower attachment member 76, support wall 77, left lower leg 78 and lower slot 79.

A left integral hinge segment 81, comprising a lower edge and an upper edge, projects upward from the junction of the rear surface of and the upper surface of left lower leg 78. A right integral hinge segment 82 projects upward from the junction of the rear surface of and the upper surface of support wall 77.

A left upper leg 83, comprising a rear surface, an upper surface and a lower surface, projects upward from the upper edge of left integral hinge segment 81 at the junction of the rear surface of and the lower surface of left upper leg 83. A right upper leg 84, comprising a rear surface, a lower surface and an upper surface, projects upward from upper edge of right integral hinge segment 82 at the junction of the rear surface of and the lower surface of right upper leg 84. A horizontal rectangular upper attachment member 85 projects forward from the upper surface of left upper leg 83 and the upper surface of right upper leg 84, upper attachment member 85 being parallel to lower attachment member 76, all directions being judged with lower attachment member 76 and upper attachment member 85 lying parallel. An upper slot 86 lies in upper attachment member 85, open at the front surface of upper attachment member 85 and extending rearward, ending in a semicircular surface, the semicircular surface of upper slot 86 being coaxial with the semicircular surface of lower slot 79.

Figure 1B:
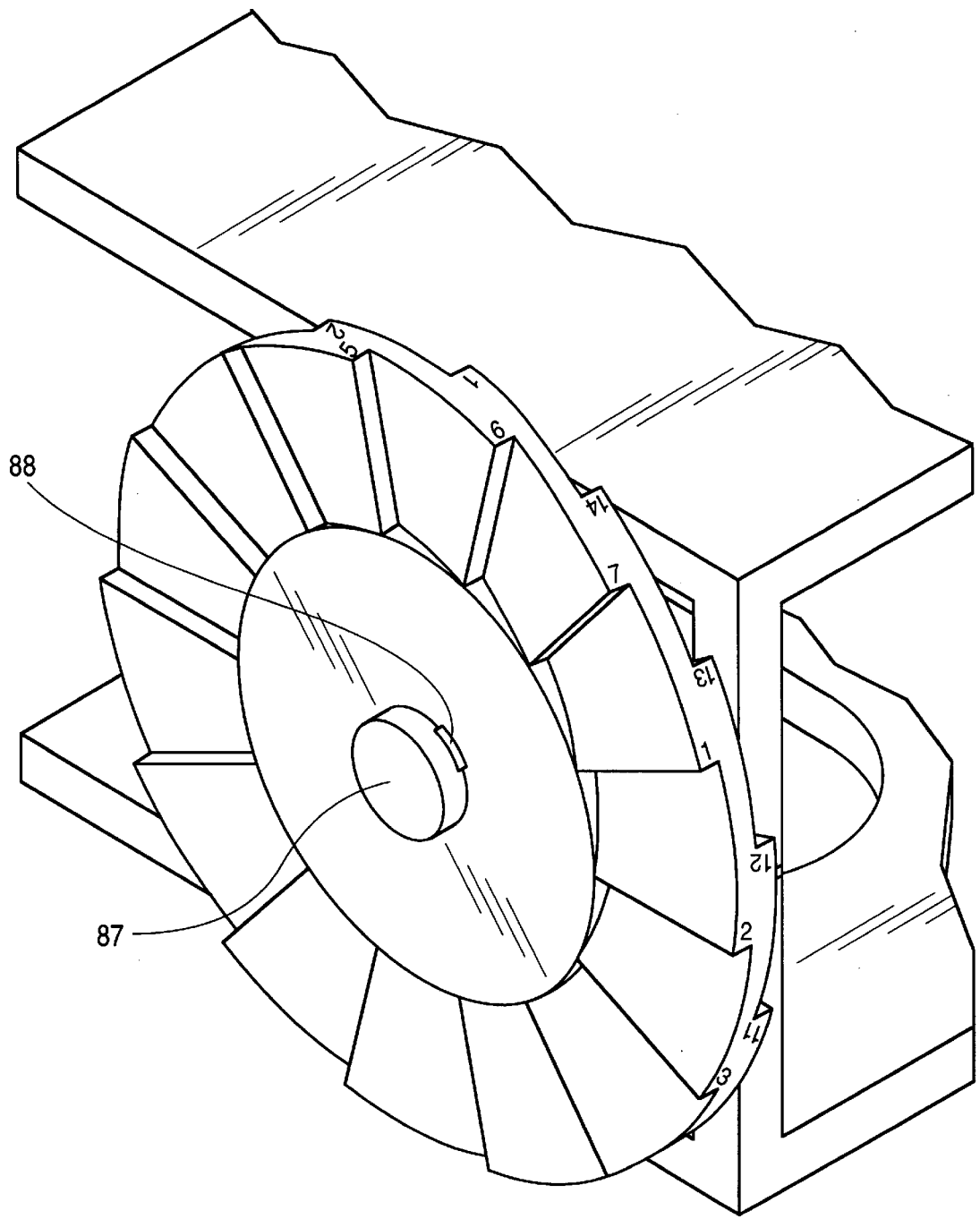
FIG. 1B depicts the rotary mechanism of the preferred embodiment of the invention from an alternate perspective, for further clarity.

A cylindrical journal member 87, this particular feature being indicated on FIG. 1B, projects horizontally outward from the right surface of support wall 77, adjacent to the upper surface of support wall 77, having its axis horizontal, comprising a distal end. Retaining means 88, projects radially outward from the distal end of journal member 87. Trapezoidal forward indexing means 89 extends rightward from the right surface of upper attachment member 85.

Upper clip member 90 comprises left upper leg 83, right upper leg 84, upper attachment member 85 and upper slot 86.

An indicator member 91 is raised on the upper surface of upper attachment member 85, pointing toward the edge of upper attachment member 85 near forward indexing means 89. Trapezoidal means to prevent reverse rotation 92 projects horizontally rightward from the right surface of support wall 77, adjacent to the rear surface of support wall 77.

A gripping unit 93 is a single part molded of firm flexible plastic material and comprises lower attachment member 76, support wall 77, left lower leg 78, lower slot 79, left integral hinge segment 81, right integral hinge segment 82, left upper leg 83, right upper leg 84, upper attachment member 85, upper slot 86, journal member 87, retaining means 88, forward indexing means 89, indicator member 91 and means to prevent reverse rotation 92.

Lower attachment member 76, lower slot 79, upper attachment member 85, and upper slot 86 have dimensions, finishes and locations such that, simultaneously, lower slot 79 can be manually forced onto the neck of bottle member 1 and upper slot 86 can be manually forced onto the cylindrical surface of least diameter of nozzle cap member 4, with interference for retention, while nozzle cap member 4 is in the snapped-on position, and such that left integral hinge segment 81 and right integral hinge segment 82 allow nozzle cap member 4 to snap off of and swing clear of nozzle member 3 with the exertion of upward manual force on upper attachment member 85.

A disc member 94 comprises a first planar surface, a second planar surface parallel to the first planar surface, an axis perpendicular to the first planar surface, a circumferential outer surface centered about this axis and a cylindrical hole, centered about this axis. A first ratchet tooth set 95 comprises fourteen contiguous, equally spaced, axial ratchet teeth, each tooth protruding from the first planar surface of disc member 94, in a direction parallel to the axis of the cylindrical hole of disc member 94. A first set of equally spaced sequential symbols 96 comprising the fourteen equally spaced, sequential Arabic numerals "1" through "14" is raised, arranged along the circumferential surface of disc member 94, each numeral being adjacent to one tooth of first ratchet tooth set 95 and having its left side closest to the adjacent tooth of first ratchet tooth set 95. A second ratchet tooth set 97 comprises fourteen contiguous, equally spaced, axial ratchet teeth, each tooth protruding from the second planar surface of disc member 94 in a direction parallel to the axis of the cylindrical hole of disc member 94. A second set of equally spaced sequential symbols 98 comprising the fourteen equally spaced, sequential Arabic numerals "1" through "7", then "1" through "7" is raised, arranged along the circumfrencial surface of disc member 94, each numeral being adjacent to one tooth of second ratchet tooth set 97 and having its left side closest to the adjacent tooth of second ratchet tooth set 97. An indicator disc member 99 is a single part molded of firm flexible plastic material and comprises disc member 94, first ratchet tooth set 95, first set of equally spaced sequential symbols 96, second ratchet tooth set 97 and second set of equally spaced sequential symbols 98.

Gripping unit 93 and indicator disc member 99 have dimensions, finishes and locations such that indicator disc member 99 may be pressed onto journal member 87 and retained by retaining means 88, allowing a slid fit for relative rotation of these parts. Indicator disc member 99 may be manually removed, flipped over and reinstalled on journal member 87.

First ratchet tooth set 95, second ratchet tooth set 97 and means to prevent reverse rotation 92 have dimensions, finishes and locations such that indicator disc member 99 is restricted from reverse rotation.

Forward indexing means 89, indicator member 91, means to prevent reverse rotation 92, first ratchet tooth set 95, first set of equally spaced sequential symbols 96, second ratchet tooth set 97, and second set of equally spaced sequential symbols 98 have dimensions, finishes and locations such that, when upper attachment member 85 is raised from the horizontal, closed position to a position approximately vertical, forward indexing means 89 first rotates indicator disc member 99, causing the juxtaposed tooth of first ratchet tooth set 95 or second ratchet tooth set 97 to slide over means to prevent reverse rotation 92, allowing means to prevent reverse rotation 92 to fall into the following space, journal member 87 being flexible to allow adequate deflection of indicator disc member 99, forward indexing means 89 abandoning indicator disc member 99 immediately thereafter. When upper attachment member 85 is manually pressed back down into a position parallel to lower attachment member 76, a position maintained by snapping nozzle cap member 4 onto nozzle member 3, forward indexing means 89 slides over the juxtaposed tooth of first ratchet tooth set 95 or second ratchet tooth set 97 and falls into the following space, reverse rotation being prohibited by the relative positions of means to prevent reverse rotation 92 and first ratchet tooth set 95 or second ratchet tooth set 97. Upon completion of this procedure, one fourteenth of a rotation has occurred and indicator member 91 points toward the next sequential element of first set of equally spaced sequential symbols 96 or second set of equally spaced sequential symbols 98.

Indicating means comprises indicator member 91, first set of equally spaced sequential symbols 96 and second set of equally spaced sequential symbols 98.

OPERATION OF THE PREFERRED EMBODIMENT

The present invention in its preferred embodiment may be used, among other ways, in displaying a transient record of instillation of therapeutic eye drops, used once per day, thereby reducing the user's dependence upon memory and allowing automatic confirmation of accurate dosing over the course of either one week or two weeks, depending upon which way indicator disc member 99 is flipped. Resetting the position of indicator disc member 99 may be executed by repeated opening and closure of the assembly or by manual rotation of indicator disc member 99.

The present invention in its preferred embodiment may also be used, among other ways, in the care of contact lenses, often prescribed for waking-hours-only wear with nightly removal, cleaning and storage, with an additional enzyme cleaning every seventh day. The contact lens storage solution bottle apparatus is opened and closed once per night, each opening indexing indicator disc member 99 by one tooth of second ratchet tooth set 97. When, in preparing to perform the nightly cleaning, the wearer sees that indicator member 91 is aligned with one of the characters "7" of second set of equally spaced sequential symbols 98 prior to removing nozzle cap member 4, with indicator disc member 99 flipped so that second ratchet tooth set 97 faces forward indexing means 89, the wearer is thereby prompted to perform the additional enzyme cleaning procedure. On the following night a character "1" of second set of equally spaced sequential symbols 98 is observed, prior to removing nozzle cap member 4, and so on, until the second character "7" of second set of equally spaced sequential symbols 98 is indicated, prior to removing nozzle cap member 4, thereby instigating the next enzyme cleaning.

CONCLUSION, RAMIFICATIONS AND SCOPE OF THE INVENTION

A removably attachable automatic squeeze-bottle utilization cycle counting device provides a convenient, simple-to-use and reliable method of keeping track of the number of times a squeeze-bottle containing a liquid, such as a liquid pharmaceutical agent or contact lens solution, has been either opened or closed in a given time period, or as a running total, or by association, the number of times another activity has been performed. This is a function heretofore accomplished by memory, calendars and paper records, often resulting in inadvertent significant noncompliance with prescribed regimens. The parts of the described embodiment of the invention are simple and can be produced and assembled economically. The invention allows for improved hygiene by decreasing the risk of digital contamination of the nozzle tip and thereby of the contents. It serves to facilitate removal of the nozzle cap, providing greater assurance that the nozzle cap will be used in the manner intended, so as to further decrease the risk of contamination.

While the above description contains many specificities, these should not be construed as limitations on the scope of the invention, but rather as exemplifications of some practical embodiments thereof. Many other variations are possible. Several examples follow. The set of symbols could be replaced with a spiral line. Various words, shapes, icons and colors could be used to alert the user to the condition of the mechanism. The simple hinges could be replaced with spring-back hinges, which provide angular location in an open position. Various other mechanisms could be utilized for the purpose of rotating the disc member. The disc member could be replaced with a rotatable object of a different shape, such as a triangle or a pointer. A secondary mechanism could be incorporated so as to flag the user that a disc member cycle has been completed. The device could bear surfaces for the display of advertising information. Means to prevent reapplication of the nozzle cap to the nozzle at the end of a disc cycle in the absence of manual intervention could be incorporated. The bottle could have any of a variety of shapes. The bottle and the cap could be molded as a single part. The attachment of the device to the existing cap could be permanent, requiring that it be discarded with each bottle of solution utilized. The ratchet tooth set could be located on the upper attachment member or on the lower attachment member and the forward indexing means and the means to prevent reverse rotation of the disc could be located on the disc. The disc could have a ratchet tooth set on one side only. The upper clip and the lower clip could attach by snapping on from above. The hinge could incorporate an angular location leaf, for holding the upper part of the unit in the open position during use. The numeric symbols could be replaced by verbiage indicating the days of the week. Accordingly, the scope of the invention should be determined not by the embodiments illustrated, but by the appended claims and their legal equivalents.

I claim as new the following:

1. A resealable liquid containment and dispensing apparatus, for the automatic recording of the number of controlled serial dispensings of liquid, performed or yet to be performed, in a given cycle, comprising:

a necked, manually deformable bottle member;

a bottle cap member, attached and sealed to said bottle member;

a nozzle member, formed on said bottle cap member and a hole passing through said nozzle member and said bottle cap member;

a nozzle cap member, removably sealable onto said nozzle member, providing, while said nozzle cap member is sealed onto said nozzle member, the isolation of said nozzle member and said liquid contents from the outside environment, and allowing, when said nozzle cap member is removed from said nozzle member, the controlled expulsion of said liquid contents through said nozzle member by the generation of positive internal fluid pressure, through manual deformation of said bottle member;

a lower clip member, removably attached to one of said bottle member and said bottle cap member;

an upper clip member, removably attached to said nozzle cap member;

a hinge, hinging said lower clip member to said upper clip member, permitting controlled removal of said nozzle cap member from and resealing of said nozzle cap member to said nozzle member in an arcuate path;

a journal member, protruding from one of said lower clip member and said upper clip member;

a disc member, rotatably retained upon said journal member;

a ratchet tooth set, comprising multiple ratchet teeth, projecting from said disc member, said ratchet teeth positioned on equal angular spaces, the number of said spaces being at least equal to the number of said ratchet teeth present;

forward indexing means protruding from the other of said lower clip member and said upper clip member as does said journal member, said forward indexing means resting between two teeth of said ratchet tooth set while said nozzle cap member is sealed to said nozzle member, providing forward rotation of said disc member through an angle equal to one of said equal angular spaces when said nozzle cap member is lifted away from and returned onto said nozzle member so as to allow free expulsion of said liquid contents from said nozzle member and subsequent resealing;

means to prevent reverse rotation protruding from the same one of said lower clip member and said upper clip member as does said journal member, said means to prevent reverse rotation resting between two teeth of said ratchet tooth set;

indicating means comprising a circularly arranged set of equally spaced sequential symbols and an indicator, said indicating means being on the surface of said disc member and one of said lower clip member and said upper clip member.

2. The apparatus of claim 1 wherein said symbols comprise verbiage indicating the days of the week.

3. The apparatus of claim 1 wherein said symbols comprise integers.

4. The apparatus of claim 1 wherein said hinge is stressed to spring to the open position when said nozzle cap member is detached from said nozzle member.

* * * * *